(12) United States Patent
Chuang et al.

(10) Patent No.: US 9,259,450 B2
(45) Date of Patent: Feb. 16, 2016

(54) USE OF A FERMENTED SOY EXTRACT AS A PREBIOTIC COMPOSITION

(75) Inventors: Ming-Hong Chuang, Taipei County (TW); Cheng Der Tony Yu, Anaheim City, CA (US); Kung-Ming Lu, Taipei (TW)

(73) Assignee: MICROBIO CO., LTD., Taipei (TW)

( * ) Notice: Subject to any disclaimer, the term of this patent is extended or adjusted under 35 U.S.C. 154(b) by 592 days.

(21) Appl. No.: 13/186,956

(22) Filed: Jul. 20, 2011

(65) Prior Publication Data

US 2012/0058104 A1    Mar. 8, 2012

Related U.S. Application Data

(60) Provisional application No. 61/365,887, filed on Jul. 20, 2010.

(51) Int. Cl.
    *A61K 35/00* (2006.01)
    *A61K 36/48* (2006.01)
    *A61K 31/43* (2006.01)

(52) U.S. Cl.
    CPC ............ *A61K 36/48* (2013.01); *A61K 31/43* (2013.01); *A61K 2035/115* (2013.01)

(58) Field of Classification Search
    None
    See application file for complete search history.

(56) References Cited

U.S. PATENT DOCUMENTS

2002/0182274 A1 * 12/2002 Lu .................................. 424/757

OTHER PUBLICATIONS

Joan Gavaldà et al. "Efficacy of Ampicillin plus Ceftriaxone in Treatment of Experimental Endocarditis Due to Enterococcus faecalis Strains Highly Resistant to Aminoglycosides" Antimicrob. Agents Chemother. 1999, 43(3):639.*
Hughes et al. "2002 Guidelines for the Use of Antimicrobial Agents in Neutropenic Patients with Cancer" Clinical Infectious Diseases 2002; 34:730-51.*

* cited by examiner

*Primary Examiner* — Thane Underdahl
(74) *Attorney, Agent, or Firm* — WPAT, P.C.; Anthony King (57) ABSTRACT

The present invention relates to use of a fermented soy extract as a prebiotic composition to protect beneficial bacteria in the gastrointestinal tract of an animal. Particularly, the fermented soy extract of the invention exhibits the prebiotic activity even under an antibiotic treatment. Also disclosed is combined use of an antibiotic and the fermented soy extract of the invention, which has advantages over administration of the antibiotic alone, such as decreasing the effective dose of the antibiotic and/or reducing side effects resulting from the antibiotic treatment.

14 Claims, 4 Drawing Sheets

USE OF A FERMENTED SOY EXTRACT AS A PREBIOTIC COMPOSITION

This application claims the benefit of U.S. Provisional Application No. 61/365,887, filed Jul. 20, 2010, which is incorporated herein by reference in its entirety.

FIELD OF THE INVENTION

The present invention relates to use of a fermented soy extract as a prebiotic composition to support the growth or maintenance of beneficial bacteria in the gastrointestinal tract of an animal. Particularly, the fermented soy extract of the invention exhibits the prebiotic activity even under antibiotic treatment. The present invention also relates to combined use of an antibiotic and the fermented soy extract of the invention.

BACKGROUND OF THE INVENTION

Probiotics, also called beneficial bacteria, can provide beneficial effects to the hosts such as maintaining a normal host gastrointestinal microflora and increasing resistance against pathogenic bacteria. Particular ingredients are known to support the growth or maintenance of beneficial bacteria so as to modify gastrointestinal microbial community in a beneficial manner. Such ingredients are called "prebiotics." Typical examples of known prebiotics are oligosaccharides such as fructooligosaccharides and inulin.

Antibiotics have been used to treat infections of pathogenic bacteria for many years. However, antibiotics may also kill beneficial bacteria and therefore adversely affect microbial balance in the gastrointestinal tract, which may in turn lead to an adverse gastrointestinal effect, such as diarrhea (i.e. antibiotic-associated diarrhea, AAD), stomachache, and abdominal cramp.

BRIEF SUMMARY OF THE INVENTION

The present invention is based on the unexpected finding that a fermented soy extract can be used as a prebiotic composition to support the growth or maintenance of beneficial bacteria in the gastrointestinal tract of an animal. In particular, it is found that the fermented soy extract of the invention supports the growth or maintenance of beneficial bacteria even under antibiotic treatment. It is also found that co-administration of an antibiotic with the fermented soy extract of the invention has advantages over administration of the antibiotic alone, such as decrease of the effective dose of the antibiotic and/or reduction of side effects resulting from the antibiotic treatment.

Accordingly, the present invention provides a method for supporting the growth or maintenance of beneficial bacteria in the gastrointestinal tract in an animal in need thereof comprising administering to the animal a fermented soy extract in an amount effective to support the growth or maintenance of the beneficial bacteria in the gastrointestinal tract. Particularly, the fermented soy extract is made by fermentation of an aqueous soy bean extract with at least one lactic acid bacteria e.g. a *Lactobacillus* species and optionally at least one yeast e.g. a *Saccharomyces* species.

In some embodiments of the invention, the beneficial bacteria are selected from the group consisting of *Lactobacillus, Bifidobacterium, Enterococcus, Pseudomonas, Sporolactobacillus, Micromonospora, Micrococcus, Rhodococcus, Escherichia* and any combinations thereof.

In one particular embodiment of the invention, the animal undergoes an antibiotic treatment. In a certain example, the antibiotic treatment involves administration of one or more beta-lactam antibiotics, such as ampicillin (AMP), amoxicillin (AMO) or a combination thereof, to the animal.

The present invention also provides a pharmaceutical composition comprising a fermented soy extract and an antibiotic.

Also provided is a method for administering an antibiotic, comprising administering to a patient in need thereof a therapeutically effective amount of the antibiotic in combination with a fermented soy extract.

Also provided is the use of a fermented soy extract for the manufacture of a prebiotic composition as a medicament, food additive or health care product for supporting the growth or maintenance of beneficial bacteria in the gastrointestinal tract of an animal, or as an adjuvant to be administrated with an antibiotic, for decreasing the effective dose of an antibiotic and/or reducing side effects resulting from the antibiotic treatment.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

In one aspect, the present invention provides a method for supporting the growth or maintenance of beneficial bacteria in the gastrointestinal tract in an animal in need thereof comprising administering to the animal a fermented soy extract in an amount effective to support the growth or maintenance of the beneficial bacteria in the gastrointestinal tract.

Specifically, a fermented soy extract as used herein refers to an extract made by fermentation of an aqueous soy bean extract with at least one lactic acid bacteria and optionally at least one yeast. In one embodiment, the at least one lactic acid bacteria is a *Lactobacillus* species and the at least one yeast is a *Saccharomyces* species. In certain embodiments, the fermentation is carried out using a heterogeneous culture of *Lactobacillus*, for example, a culture of 5, 10, 15, 20, 25 or 30 strains of *Lactobacillus*, and preferably, at least one yeast is added to the heterogeneous culture of *Lactobacillus*. The strains of *Lactobacillus* that can be used in the fermentation include, but are not limited to, *Lactobacillus acidophilus* CCRC (Bioresource Collection and Research Center at Food Industry Research and Development, Taiwan) 10695, 14026, 14064, 14065 and/or 14079, *Lactobacillus delbrueckii bulgaricus* CCRC 10696, 14007, 14009, 14010, 14069, 14071, 14098 and/or 16054, *Lactobacillus lactis lactis* CCRC 10791, 12267, 12306, 12312, 12315, 12323, 14016, 14015 and/or 14117, *Lactobacillus kefir* CCRC 14011, and/or *Lactobacillus kefuranofaciens* CCRC 16059. The yeast strains that can be used in the fermentation include, but are not limited to, *Saccharomyces cerevisiae* CCRC 20577, 20578, 20581, 21494, 21550, 21797, 21805, 22138, 22234, 22337, 22731 and/or 22728, and/or *Candida kefyr* CCRC 21269, 21742 and/or 22057. Specifically, the fermentation is followed by one or more steps such as sterilization, filtration, concentration, lyophilization or any combinations thereof. Preferably, the fermentation is followed by sterilization, e.g. by heat, with optional filtration and concentration. More preferably, the fermented soy extract can be dried, e.g. via lyophilization, to obtain the fermented soy extract in a powder form. In a certain embodiment, the fermented soy extract of the invention is made by a process comprising the steps of (a) fermenting an aqueous soy bean extract with at least one lactic acid bacteria and together with at least one yeast to form a fermented liquid; (b) sterilizing said fermented liquid; (c) filtering said sterilized fermented liquid; and (d) removing water from said filtered fermented liquid to form a concentrated fermented soy extract. A fermented soy extract as used herein can be prepared as in U.S. Pat. Nos. 6,855,350 and 6,733,801, each of which is hereby incorporated by reference in its entirety.

The term "animal" or "patient" as used herein includes humans and non-human animals such as companion animals (e.g., dogs, cats, and the like), farm animals (e.g., cows, sheep, pigs, horses, and the like) or laboratory animals (e.g., rats, mice, guinea pigs, and the like).

The term "probiotics" or "beneficial bacteria" as used herein refers to live microorganisms thought to be healthy for the host individuals. According to the currently adopted definition by the World Health Organization (WHO), probiotics are: "live microorganisms which when administered in adequate amounts confer a health benefit on the host", including lactic acid bacteria (LAB) and bifidobacteria, which are the most common types of microbes as probiotics. Specifically, in some embodiments of the invention, the beneficial bacteria include the *Lactobacillus* genus e.g. *L. rhamnosus, L. acidophilus, L. crispatus, L. fermentum, L. plantarum, L. casei, L. paracasei, L. jensenii, L. gasseri, L. cellobiosis, L. brevis, L. delbrueckii, L. rogosae* and *L. bifidum*; the *Bifidobacterium* genus e.g. *B. bifidum, B. breve, B. adolescentis, B. infantis, B. pseudolongum, B. angulatum, B. catenulatum* and *B. longumt*; the *Enterococcus* genus e.g. *E. faecium* and *E. thermophilus*, the *Pseudomonas* genus e.g. *P. aeruginosa, P. putida, P. cepacia,* and *P. fluorescens*; the *Sporolactobacillus* genus; the *Micromonospora* genus; the *Micrococcus* genus; the *Rhodococcus* genus and the *Escherichia* genus e.g. *E. coli*.

An "effective amount" or an "effective dose," in connection with administration of a biologically active agent, indicates an amount or dose of the biologically active agent that is sufficient to result in an intended biological effect in a treated animal in comparison to an untreated control animal, such as supporting the growth or maintenance of beneficial bacteria, reducing, attenuating or eliminating at least one symptom or condition of the disease being treated e.g. decreasing cell number of pathogenic bacteria, or reducing side effects resulting from a therapy. Effective amounts vary, as recognized by those skilled in the art, depending on route of administration, excipient usage, and the age, size, and condition of the subject to be treated. Precise amounts of a pharmacological agent required to be administered depend on the judgment of the practitioner and are peculiar to each individual.

When used herein, the term "supporting the growth or maintenance of beneficial bacteria" or any variations thereof, can encompass, for example, an increase, promotion or stimulation, or maintenance or preservation of the cell number, function or activity of the beneficial bacteria in response to treatment of a biological active agent at an effective dose, as compared to a control without the treatment. Specifically, the term can include, for example, an increase of the cell number of beneficial bacteria by about 1-fold, 2-fold, 4-fold, 6-fold, 8-fold, 10-fold, 20-fold, 40-fold, 60-fold, 80-fold, 100-fold or more, by treatment of a fermented soy extract according to the invention, as compared to a control without the treatment.

The fermented soy extract of the invention may be delivered through any physiologically acceptable route such as orally, parentally (e.g. intramuscularly, intravenously, subcutaneously, intraperitoneally), transdermally, rectally, by inhalation and the like. In one embodiment, the fermented soy extract of the invention is orally administered.

To facilitate delivery, the fermented soy extract according to the invention may be formulated into a composition with a physiologically acceptable carrier. The composition of the invention can be formulated as a medicament, food additive or health care product.

"Physiologically acceptable" as used herein means that the carrier is compatible with the active ingredient contained in the composition, preferably capable of stabilizing the active ingredient, and not deleterious to the subject to be treated. The carrier may serve as a diluent, vehicle, excipient, or medium for the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical composition can additionally include lubricating agents such as talc, magnesium stearate, and mineral oil; wetting agents; emulsifying and suspending agents; preserving agents such as methyl- and propylhydroxy-benzoates; sweetening agents; and flavoring agents.

The composition of the invention can be prepared in any forms as desired using conventional techniques in view of the teachings provided in the specification. In certain examples, the composition according to the invention can be prepared in the form of tablets, pills, powders, lozenges, sachets, cachets, elixirs, suspensions, emulsions, solutions, syrups, soft and hard gelatin capsules, suppositories, sterile injectable solutions, and packaged powders.

The composition of the invention may be delivered through any physiologically acceptable route such as orally, parentally (e.g. intramuscularly, intravenously, subcutaneously, interperitoneally), transdermally, rectally, by inhalation and the like. In one embodiment, the composition of the invention is orally administered.

In this invention, it is found that the fermented soy extract exhibits prebiotic activity to support the growth or maintenance of beneficial bacteria in the gastrointestinal tract of an animal. Surprisingly, when compared with known prebiotics, such as fructooligosaccharides or inulin, the fermented soy extract of the invention exhibits significantly higher prebiotic activity to support the growth or maintenance of beneficial bacteria. See examples below.

More surprisingly, it is found that the fermented soy extract of the invention exhibits the prebiotic activity to support the growth or maintenance of beneficial bacteria even under treatment of antibiotics, indicating that the fermented soy extract of the invention can effectively protect beneficial bacteria from damage caused by the treatment of antibiotics and keep them survival and/or even further promote their growth under the antibiotic treatment.

Accordingly, in one embodiment, the fermented soy extract of the invention is administered to an animal undergoing antibiotic treatment, whereby the beneficial bacteria in the gastrointestinal tract of the animal is protected from the possible damage caused by the antibiotic treatment and therefore the side effects resulting from the antibiotic treatment such as diarrhea, stomachache, and abdominal cramp may be reduced or prevented.

The term "antibiotic treatment" or "antibiotic therapy" as used herein refers to any treatment or therapy using an antibiotic. Classes of antibiotics that can be used include, but are not limited to, macrolides (i.e., clarithromycin and erythromycin), penicillins (i.e., nafcillin, ampicillin, amoxicillin), cephalosporins (i.e., cefazolin), carbepenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate). Examples of specific antibiotics that can be used in the invention include, but are not limited to, erythromycin, nafcillin, ampicillin, amoxicillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. In one embodiment of the invention, the antibiotic treatment involves administering to an animal one or more beta-lactam antibiotics, such as ampicillin, amoxicillin or both.

According to the invention, the fermented soy extract can be administered simultaneously (concurrently) or sequentially with the antibiotic treatment. Specifically, the fermented soy extract is administered prior to or after the antibiotic treatment or simultaneously with the antibiotic treatment.

By another aspect, the present invention provides a pharmaceutical composition comprising a fermented soy extract and one or more antibiotics. In one embodiment, the pharmaceutical composition of the invention comprises a fermented soy extract and one or more beta-lactam antibiotics. Typical examples of the beta-lactam antibiotics include but are not limited to ampicillin and amoxicillin.

Also provided in the present invention is a method for administering an antibiotic, comprising administering to a patient in need thereof a therapeutically effective amount of the antibiotic in combination with a fermented soy extract. According to the present invention, the combined use of an antibiotic and the fermented soy extract of the invention has advantages over administration of the antibiotic alone, which at least include decreasing the effective dose of the antibiotic and/or reducing side effects resulting from the antibiotic treatment.

Specifically, in some embodiments of the invention, the effective dose of the antibiotic, when used in combination with the fermented soy extract of the invention, is about 90% or less, 80% or less, 70% or less, 60% or less, 50% or less, 40% or less, 30% or less, 20% or less, 10% or less, of the dose of the antibiotic when used alone. In a certain example of the invention, the effective dose of an antibiotic, when used in combination with the fermented soy extract of the invention, is about 10% or less of the dose of the antibiotic when used alone. In some embodiments of the invention where two or more antibiotics are involved, these antibiotics, when used together with the fermented soy extract of the invention, are administered in a total amount effective to treat a patient's condition treatable by these antibiotics, which is lower than the total amount of these antibiotics when used without the fermented soy extract.

According to the invention, administration of an antibiotic with the fermented soy extract of the invention can reduce side effects resulting from the antibiotic treatment. In certain embodiment, the side effect is an adverse gastrointestinal effect caused by abnormal microbial balance in the gastrointestinal tract due to the antibiotic treatment, including but are not limited to diarrhea, stomachache, abdominal cramp and any combinations thereof.

The present invention will now be described more specifically with reference to the following embodiments, which are provided for the purpose of demonstration rather than limitation.

EXAMPLE 1

Stimulation of Growth of Beneficial Bacteria by the Fermented Soy Extract of the Invention 1.1 Materials A fermented soy bean extract was produced as described in U.S. Pat. Nos. 6,855,350 and 6,733,801, the contents of which are hereby incorporated by reference in their entirety. Briefly, soybeans were mixed with distilled water and the mixture was heated and filtered. The aqueous soy extract thus obtained was fermented with at least one lactic acid bacteria and at least one yeast, and the fermented extract was sterilized, filtered and concentrated to obtain a fermented soy extract in a concentrated form. The resulted fermented soy bean extract was analyzed for its prebiotic activity and compared with three commercial prebiotic products i.e. an inulin product from Warcoing Industrie SA and two fructooligosaccharide products from Warcoing Industrie SA, and Taiwan Sugar Corporation, respectively.

*B. infantis*, *B. lactis* Bb-12 and *B. longum* were purchased from the Bioresource Collection and Research Center (BCRC) at Food Industry Research and Development Institute (FIRDI) (Hsinchu, Taiwan R.O.C.). *B. infantis* was cultured in MRS medium containing 0.05% cycteine-HCl, and *B. lactis* Bb-12 and *B. longum* were cultured in Bifidobacteria Iodoacetate Medium-25 (BIM-25).

Artificial gastric juice was prepared by dissolving 0.3% pepsin in 0.5% NaCl and adjusting pH to 2.0 by 1N HCl. Artificial intestinal juice was prepared by dissolving 0.1% pancreatin in 0.5% NaCl and adjusting pH to 8.0 by 1N NaOH.

1.2 Method

To conduct the assay, the fermented soy bean extract and the three commercial prebiotic products, as described above, were diluted as in Table 1.

TABLE 1

| Samples | Major ingredients | Dilution and filtration |
|---|---|---|
| FSE (1 ml) | fermented soy bean extract | 1 ml of the fermented soy bean extract as described above was diluted in distilled water to a final volume of 200 ml. 6 ml of the diluted sample was tested in the probiotic activity assay. |
| Inulin (Warcoing Industrie SA) | inulin | 10 g$^1$ of an inulin product (Warcoing Industrie SA) was added to distilled water to a final volume of 200 ml. 6 ml of the diluted sample was tested in the probiotic activity assay. |
| Fructooligo-saccharide (Warcoing Industrie SA) | fructooligo-saccharide | 10 g$^1$ of a fructooligosaccharide product (Warcoing Industrie SA) was added to distilled water to a final volume of 200 ml. 6 ml of the diluted sample was tested in the probiotic activity assay. |
| Fructooligo-saccharide (Taiwan Sugar Corporation) | fructooligo-saccharide | 12.5 g$^1$ of a fructooligosaccharide product (Taiwan Sugar Corporation) was added to distilled water to a final volume of 200 m. 6 ml of the diluted sample was tested in the probiotic activity assay. |
| Water control | distilled water | 6 ml of distilled/filtered water was taken for the probiotic activity assay. |

$^1$the suggested amount by the manufacturer.

6 ml of each of the samples was mixed with 6 ml of the artificial gastric juice and incubated with shaking (100 rpm) at 37° C. for 1 hour. Subsequently, 6 ml of the artificial intestinal juice was added to the mixture and the pH was adjusted by NaOH to a final value between 6.0 and 7.0. The artificial gastric/intestinal juice mixture with individual tested samples was then incubated at 37° C. with shaking for further 30 min (called "reaction solution" hereinafter). 1 ml of the bacteria culture ($10^7$ CFU/mL) was obtained and mixed with 9 ml of the above-mentioned reaction solution, which was then 10-fold serial diluted with distilled water. The serial-diluted solutions were incubated at 37° C. with shaking (100 rpm) for 24 hours, during which time 1 ml of the solutions was taken out at different time points (0, 4 and 24 hours) and plated in agar plate using the pour plate method in an anaerobic condition at 37° C. for 2 days. Bacteria colonies were counted. Table 2 shows the results.

TABLE 2

| | Cell number (Log CFU/mL) | | |
|---|---|---|---|
| Treatment | *B. infantis* | *B.* Bb-12 | *B. longum* |
| FSE (1 mL) | 8.050$^a$ | 8.030$^a$ | 8.230$^a$ |
| Inulin | 7.330$^b$ | 6.795$^{bc}$ | 7.445$^b$ |
| Fructooligosaccharide (Warcoing Industrie SA) | 7.170$^b$ | 7.170$^b$ | 7.445$^b$ |
| Fructooligosaccharide (Taiwan Sugar Corporation) | 7.155$^b$ | 6.975$^c$ | 6.435$^c$ |
| Blank (Water) | 7.040$^b$ | 6.770$^c$ | 5.520$^d$ |

*Each value is expressed as mean of two individual observations. Statistical differences between different treatment group are evaluated by Tukey's Studentized Range (HSD) test. Value in the same column with different letter superscript a to d represented significant difference between two means (p < 0.05). Initial bacteria count at time zero is $10^6$ CFUs/mL.

As shown in the results, the fermented soy bean extract (FSE) of the invention exhibits prebiotic activity to support the growth or maintenance of bifidobacteria, and the prebiotic activity of the fermented soy bean extract is significantly better than that of the known prebiotic products.

Figure 1:
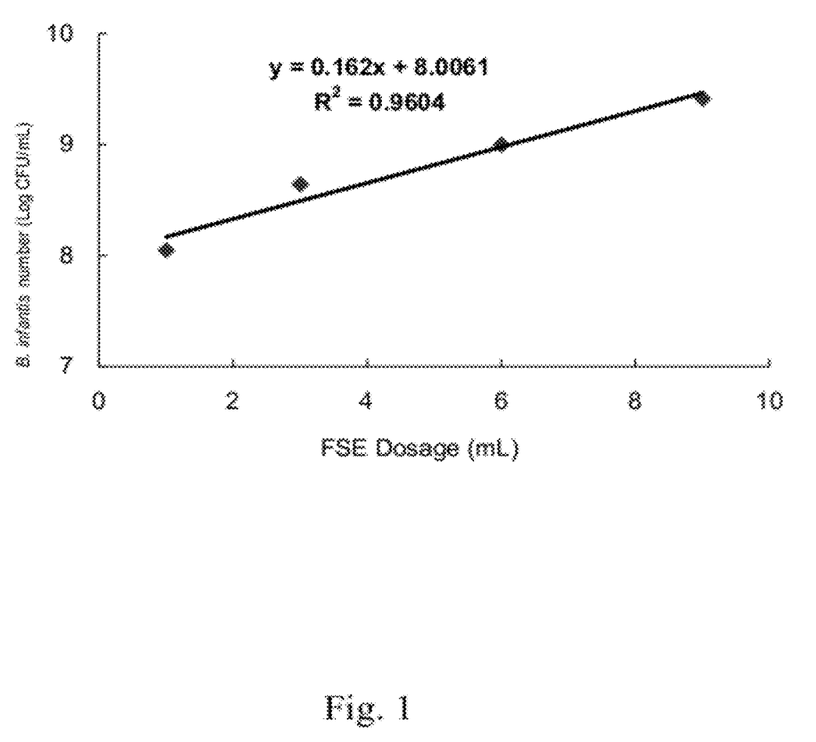
FIG. 1 shows that the fermented soy extract of the invention promotes the growth of *B. infantis* in a dose dependent manner.

In addition, different amounts of the fermented soy extract of the invention (after treatment of the artificial gastric/intestinal juice mixture) were incubated with the culture of *B. infantis* for 24 hours, and the cell number was counted. FIG. 1 shows that the fermented soy extract of the invention promotes the growth of *B. infantis* in a dose dependent manner.

EXAMPLE 2

Stimulation of Growth of Beneficial Bacteria by Fermented Soy Extract of the Invention Under Treatment of Antibiotics 2.1 Antibiotics Inhibit the Growth of *Lactobacillus* while the Fermented Soy Extract Stimulates the Growth of the Bacteria Three *Lactobacillus* strains, *L. rhamnosus* BCRC 10940, *L. paracasei* BCRC 14001, *L. delbrueckii* BCRC 14008, were purchased from the FIRDI, which were cultured in MRS w/o agar medium (Difco) and stored at 4° C. To activate the bacteria, the cells were inoculated in MRS medium at a concentration of 5% (v/v) and cultured at 37° C. for 24 hours, and then $10^7$ cells/ml of each of the three *Lactobacillus* strains was inoculated in 5 ml of MRS medium with shaking overnight.

Antimicrobial activity of antibiotics against the three *Lactobacillus* strains was measured by a microtitre plate-based method. Briefly, antibiotics of ampicillin (AMP), amoxicillin (AMO), clarithromycin (CAM) and erythromycin (Eryc) in serially descending concentrations were individually added to each well of 24-well plates and then MRS medium was added to each well to ensure that the final volume was single strength of the nutrient medium. 10 μl of activated bacterial cultures was added to each well to achieve a concentration of $10^5$ cfu/ml per well, and the plates were incubated at 37° C. for 24 h. The growth of the bacteria was measured by absorbance at 600 nm and the survival percentages were determined. Further, the minimal inhibitory concentration (MIC) was determined as the lowest concentration of the antibiotics allowing no visible growth of the bacteria. Data are the averages of a triplicate experiment. According to the results, the *Lactobacillus* strains were sensitive to the treatment of the antibiotics; the MIC values of AMP, AMO, CAM and Eryc were 3.6, 3.6, 1.0 and 1.0 μg/ml, respectively.

On the other hand, the fermented soy extract prepared of the invention as in Example 1 was analyzed for its prebiotic activity to support the growth of beneficial bacteria using the microtitre plate-based method as described above. The fermented soy extract of the invention was added at a concentration of 5% into the wells and the plates were incubated at 37° C. for 48 h. The cell number was counted. Table 3 shows the results.

TABLE 3

| Bacteria | MRS | MRS + FSE | AMP (2 μg) | AMO (2 μg) | CAM (1 μg) | Eryc (2 μg) |
|---|---|---|---|---|---|---|
| L. rhamnosus | $9.21 \times 10^8$ | $1.13 \times 10^9$ | $6.30 \times 10^4$ | $3.40 \times 10^3$ | $5.10 \times 10^4$ | $5.07 \times 10^4$ |
| L. paracasei | $2.49 \times 10^9$ | $7.52 \times 10^9$ | $3.29 \times 10^6$ | $2.00 \times 10^4$ | $3.27 \times 10^5$ | $3.18 \times 10^5$ |
| L. delbrueckii | $3.06 \times 10^9$ | $4.76 \times 10^9$ | $5.58 \times 10^6$ | $5.00 \times 10^4$ | $3.45 \times 10^5$ | $3.16 \times 10^5$ |

As shown in Table 3, the fermented soy extract of the invention stimulates the growth of Lactobacillus while the antibiotics inhibit the growth of the bacteria.

2.2 Simultaneous Treatment of Antibiotics and the Fermented Soy Extract of the Invention To each well of a 24-well plate containing $10^5$ cfu/ml of L. rhamnosus, L. paracasei and L. delbrueckii in MRS medium, the antibiotics, AMP or AMO, was added to a final concentration of 2 μg/ml or 5 μg/ml together with the fermented soy extract in a final concentration of 5%. The plates were incubated at 37° C. for 48 h. Tables 4 and 5 shows the survival counting as measured.

TABLE 4 treatment of antibiotics at 2 μg/ml together with the fermented soy extract

| Bacterial strains | AMP only | AMP + FSE | Fold of survival (AMP + FSE/AMP) | AMO only | AMO + FSE | Fold of survival (AMP + FSE/AMO) |
|---|---|---|---|---|---|---|
| L. rhamnosus | 967 ± 76 | 65000 ± 3040 | 67.2 ± 9.2 | 500 ± 50 | 49000 ± 7570 | 98.0 ± 27.7 |
| L. paracasei | 3670 ± 350 | 57300 ± 4730 | 15.6 ± 3.1 | 3000 ± 500 | 73700 ± 2020 | 24.6 ± 5.7 |
| L. delbrueckii | 4330 ± 260 | 91700 ± 6430 | 21.2 ± 2.9 | 6670 ± 610 | 104000 ± 5060 | 15.6 ± 2.4 |

TABLE 5 treatment of antibiotics at 5 μg/ml together with the fermented soy extract

| Bacterial strains | AMP only | AMP + FSE | Fold of survival (AMP + FSE/AMP) | AMO only | AMO + FSE | Fold of survival (AMP + FSE/AMO) |
|---|---|---|---|---|---|---|
| L. rhamnosus | 230 ± 15 | 39000 ± 620 | 169.6 ± 14.7 | 370 ± 10 | 46000 ± 200 | 124.3 ± 4.0 |
| L. paracasei | 4700 ± 409 | 68000 ± 551 | 14.5 ± 1.5 | 4300 ± 445 | 76000 ± 132 | 17.7 ± 2.0 |
| L. delbrueckii | 1230 ± 231 | 106000 ± 9000 | 86.2 ± 28.9 | 1170 ± 76 | 122000 ± 104 | 104.3 ± 7.3 |

The results show that by the treatment of the fermented soy extract of the invention, the survival of Lactobacillus under AMP or AMO-stressed conditions in a concentration of 2 μg/ml was increased by about 16-67 and 16-98 folds, respectively; and the survival of Lactobacillus under AMP or AMO-stressed conditions in a concentration of 5 μg/ml was increased by about 15-170 and 18-124 folds, respectively, when compared with that without the treatment of the fermented soy extract.

2.3 Pre-Treatment by the Fermented Soy Extract

Figure 2:
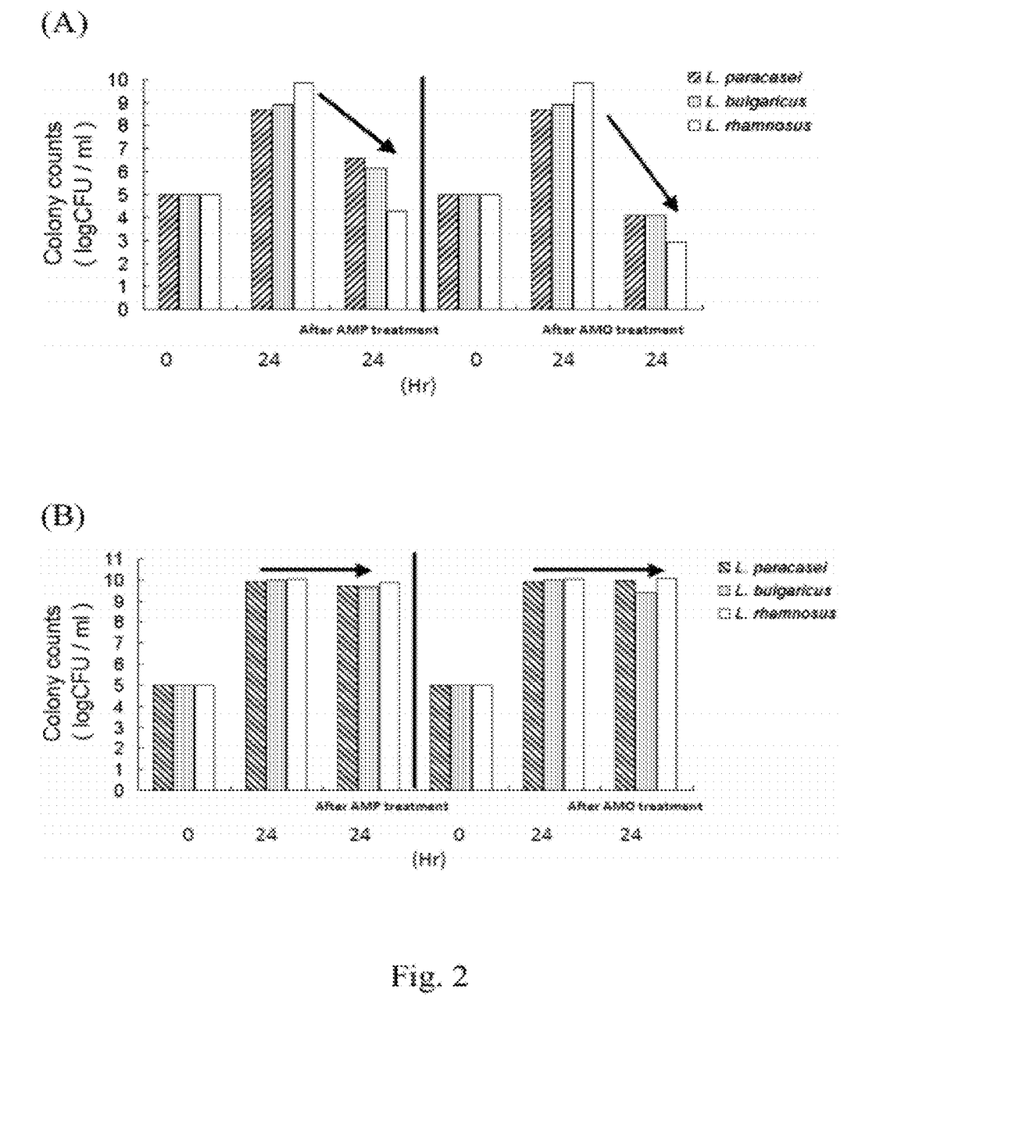
FIG. 2 shows the colony counts of the *Lactobacillus* strains after treatment of antibiotics (A) without or (B) with pre-treatment of the fermented soy extract of the invention.

To each well of a 24-well plate containing $10^5$ cfu/ml of L. rhamnosus, L. paracasei and L. delbrueckii in MRS medium, the fermented soy extract was added to a final concentration of 5% or not. The cells were then pre-incubated 37° C. for 24 h. After the pre-incubation, to each well of the plates, the antibiotics, AMP or AMO, was subsequently added in a final concentration of 5 μg/ml and the plates were incubated for further 24 h. The cell colonies were counted. FIG. 2 shows the results.

As shown in FIG. 2A, without pre-treatment of the fermented soy extract of the invention, the growth of Lactobacillus was largely inhibited by the antibiotics. In contrast, as shown in FIG. 2B, with pre-treatment of the fermented soy extract of the invention, the growth of Lactobacillus under the treatment of antibiotics was kept normal as that prior to addition of the antibiotics or even increased.

The above data demonstrates that the fermented soy extract can effectively protect Lactobacillus from the destruction caused by β-lactam antibiotics and support the growth or maintenance of the beneficial bacteria under the antibiotic treatment.

Figure 3:
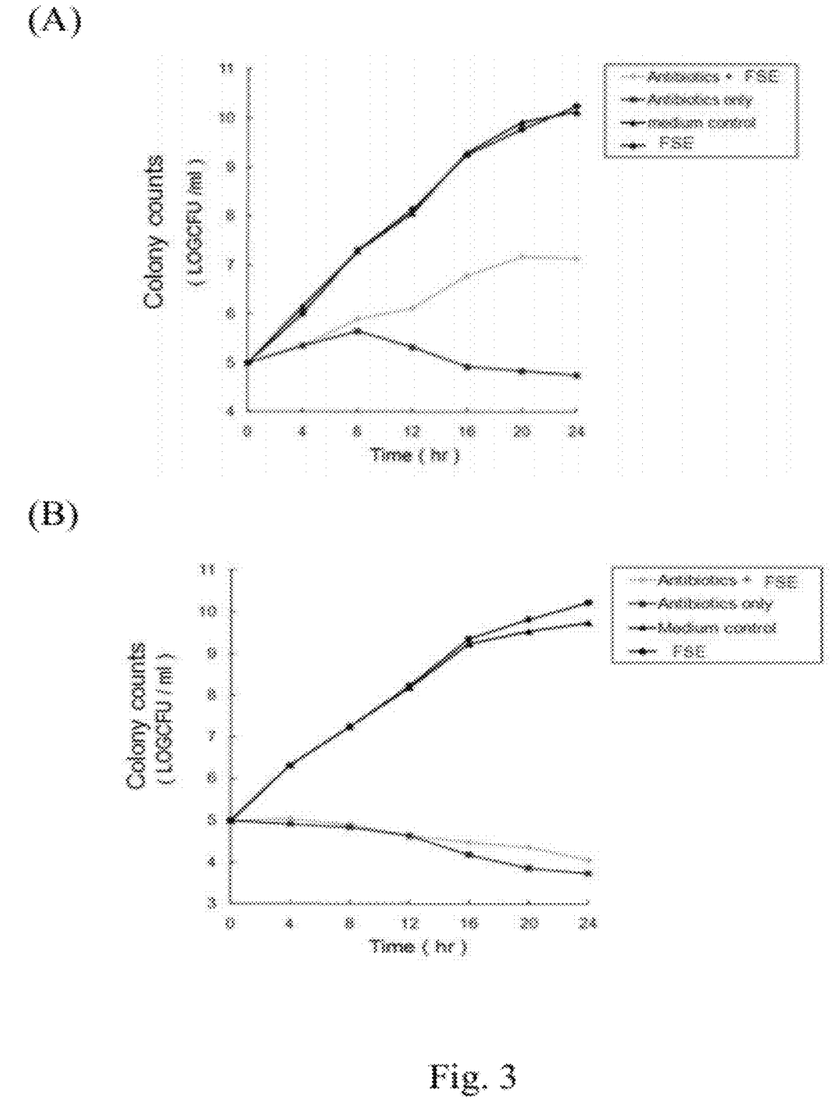
FIG. 3 shows the growth curves of (A) *L. rhamnosus*, (B) *L. paracasei*, and (C) *L. bulgaricus* under different conditions, medium only ("medium control"), medium containing the fermented soy extract of the invention ("FSE"), medium containing 5 μg/ml antibiotics AMP or AMO ("Antibiotics only"), and medium containing 5 μg/ml antibiotics AMP or AMO and the fermented soy extract of the invention ("Antibiotics+FSE").

Further, by collecting the cell number every 4 h, the growth curves of the three Lactobacillus strains were obtained as in FIG. 3. The results indicate that the fermented soy extract of the invention starts to enhance the growth of the Lactobacillus strains at about 8 h following the antibiotic treatment. The results confirm that the fermented soy extract of the invention can support the growth or maintenance of the beneficial bacteria, and among the Lactobacillus strains, the fermented soy extract of the invention shows the relatively strong prebiotic activity on L. rhamnosus.

EXAMPLE 3

Combined Use of Antibiotic(S) and the Fermented Soy Extract of the Invention in Animal Models BSK mice (about 20 g) were infected with H. pylori and confirmed by the urease assay. The animals were randomly divided into five groups; each having six mice. The animals were orally administered with CAM and AMO, with or without the fermented soy extract of the invention, or placebo alone, as follows, once a day for 7 consecutive days:

Group I: CAM+AMO, 200 mg/kg/day for each antibiotic (positive control);
Group II: CAM+AMO, 20 mg/kg/day for each antibiotic, in combination with 1% FSE;
Group III: CAM+AMO, 20 mg/kg/day for each antibiotic, in combination with 2% FSE;
Group IV: CAM+AMO, 20 mg/kg/day for each antibiotic; and
Group V: placebo (negative control).

After the 7 consecutive days of administration, the animals were maintained for another 7 days in the same condition until the test was done. During the test, stool samples were collected on day 0, 4, 8 and 14 respectively and analyzed by the urease assay (CLO test, BioLabs) or the HpSA test (*Helicobacter pylori* Stool Antigen test, Meridian Bioscience) for the presence of *H. pylori*, such as those described in *J. Ayub. Med. Coll. Abbottabad.* 15(4), 34-36. (2003), *World J. Gastroenterol.* 16(23), 2926-2930. (2010) or *World J. Gastroenterol.* 11(3), 386-388. (2005). For the CLO test, a yellow color was recorded as negative and a pink color was recorded as positive. For the HpSA test, the optical density (OD) was measured at 450 nm, wherein the OD value less than 0.14 was defined as negative and the OD value higher than 0.14 was consider positive. Table 7 shows the results.

TABLE 7

Results of the animal tests

|  | Day 0 | Day 4 | Day 8 | Day 14 |
|---|---|---|---|---|
| Group I: CAM + AMO, 200 mg/kg/day for each antibiotic | | | | |
| animal 1 | +++ | − | − | − |
| animal 2 | + | − | − | − |
| animal 3 | +++ | − | − | − |
| animal 4 | +++ | − | − | − |
| animal 5 | ++ | − | − | − |
| animal 6 | +++ | − | − | − |
| ratio | 6/6 | 0/6 | 0/6 | 0/6 |
| Group II: CAM + AMO, 20 mg/kg/day for each antibiotic, in combination with 1% FSE | | | | |
| animal 1 | + | − | − | + |
| animal 2 | + | − | − | ++ |
| animal 3 | + | + | − | ++ |
| animal 4 | + | +++ | + | ++ |
| animal 5 | + | + | + | − |
| animal 6 | + | − | − | ++ |
| ratio | 6/6 | 3/6 | 2/6 | 5/6 |
| Group III: CAM + AMO, 20 mg/kg/day for each antibiotic, in combination with 2% FSE | | | | |
| animal 1 | ++ | + | − | − |
| animal 2 | ++ | − | − | − |
| animal 3 | ++ | + | − | − |
| animal 4 | + | ++ | + | − |
| animal 5 | + | − | − | + |
| animal 6 | ++ | − | − | + |
| ratio | 6/6 | 3/6 | 1/6 | 2/6 |
| Group IV: CAM + AMO, 20 mg/kg/day for each antibiotic | | | | |
| animal 1 | + | + | + | ++ |
| animal 2 | +++ | + | ++ | ++ |
| animal 3 | ++ | +++ | − | ++ |
| animal 4 | +++ | ++ | + | ++ |
| animal 5 | + | ++ | + | ++ |
| animal 6 | +++ | + | + | ++ |
| ratio | 6/6 | 6/6 | 5/6 | 6/6 |
| Group V: placebo | | | | |
| animal 1 | +++ | + | +++ | +++ |
| animal 2 | +++ | +++ | +++ | +++ |
| animal 3 | + | +++ | +++ | +++ |
| animal 4 | + | + | +++ | +++ |

TABLE 7-continued

Results of the animal tests

|  | Day 0 | Day 4 | Day 8 | Day 14 |
|---|---|---|---|---|
| animal 5 | + | +++ | +++ | +++ |
| animal 6 | +++ | +++ | +++ | +++ |
| ratio | 6/6 | 6/6 | 6/6 | 6/6 |

"−" means a yellow color in the CLO test, or OD 450 < 0.14 in the HpSA test.
"+" means a pink color in the CLO test (<20% infection), or OD 450 at a range of 0.14-0.3 in the HpSA test.
"++" means a pink color in the CLO test (20-50% infection), or OD 450 at a range of 0.3-0.64 in the HpSA test.
"+++" means a pink color in the CLO test (>50% infection), or OD 450 > 0.64 in the HpSA test.

As shown in Table 7, in Group IV, the treatment of AMO and CAM at a low dose (20 mg/kg for each antibiotic) failed to clear *H. pylori* infection in the animals (all the animals in Group IV were found to still have *H. pylori* in the stool samples); but in Group III, the same antibiotic treatment together with 2% FSE of the invention successfully enhanced the bactericidal effect (only two animals in Group III were found to have *H. pylori* in the stool samples). In addition, observation of the stool samples from the animals in Group III showed that these stool samples looked normal (not too wet and soft). However, even though treatment of AMO and CAM at a high dose (200 mg/kg for each antibiotic) cleared up all the *H. pylori* infection in the animals (all the animals in Group I are found to have no *H. pylori* in the stool samples), the stool samples were found wet and soft, indicating that the animals in Group I suffered adverse gastrointestinal effect from the antibiotic treatment.

It is suggested that combined use of antibiotic(s) and the fermented soy extract of the invention not only can reduce the dose of antibiotic(s) but also provide protective effect on the intestinal tract of the animal and reduce side effects under the antibiotic treatment.

In conclusion, as demonstrated in the above experiments, the fermented soy extract of the invention, prepared according to the method as described in U.S. Pat. Nos. 6,855,350 and 6,733,801, can be used as a prebiotic composition to support the growth or maintenance of beneficial bacteria in the gastrointestinal tract of an animal, particularly *Lactobacillus* and *Bifidobacterium*. The prebiotic activity of the fermented soy extract of the invention is significantly better than that of some known prebiotic products in the market. Further, the prebiotic activity of the fermented soy extract of the invention can support the growth or maintenance of beneficial bacteria even under antibiotic treatment. Moreover, a combination of antibiotic(s) and the fermented soy extract of the invention provides advantages over administration of antibiotic(s) alone, such as decrease of the effective dose of antibiotic(s) and protection of the intestinal tract of the animal and reduction of side effects from the antibiotic treatment.

We claim:

1. A method for supporting the growth or maintenance of beneficial bacteria being lactic acid bacteria or bifidobacteria in the gastrointestinal tract in a human or non-human animal in need thereof by stimulating the beneficial bacteria to grow, comprising administering to the human or non-human animal a fermented soy extract as a prebiotic agent in an amount effective to stimulate the beneficial bacteria to grow, wherein the fermented soy extract is made by a process comprising the steps of (a) fermenting an aqueous soy bean extract with at least one lactic acid bacteria and together with at least one yeast to form a fermented liquid; (b) sterilizing said fermented liquid; (c) filtering said sterilized fermented liquid; and (d) removing water from said filtered fermented liquid to form a concentrated fermented soy extract.

2. The method of claim 1, wherein the at least one lactic acid bacteria used in step (a) of the process is a *Lactobacillus* species and the yeast used in step (a) of the process is a *Saccharomyces* species.

3. The method of claim 1, wherein the beneficial bacteria are *L. rhamnosus, L. paracasei, L. delbrueckii, B. infantis, B. lactis* Bb-12, or *B. longum*.

4. The method of claim 1, wherein the fermented soy extract is orally administered to the human or non-human animal.

5. The method of claim 1, wherein the human or non-human animal undergoes antibiotic treatment.

6. The method of claim 5, wherein the antibiotic treatment involves administration of a beta-lactam antibiotic to the human or non-human animal.

7. The method of claim 6, wherein the antibiotic is selected from the group consisting of ampicillin, amoxicillin and a combination thereof.

8. A method for reducing side effects resulting from antibiotic treatment in a patient, comprising administering to the patient receiving the antibiotic treatment a fermented soy extract as a prebiotic agent in an amount effective to stimulate beneficial bacteria being lactic acid bacteria or bifidobacteria to grow, wherein the fermented soy extract is made by a process comprising the steps of (a) fermenting an aqueous soy bean extract with at least one lactic acid bacteria and together with at least one yeast to form a fermented liquid; (b) sterilizing said fermented liquid; (c) filtering said sterilized fermented liquid; and (d) removing water from said filtered fermented liquid to form a concentrated fermented soy extract.

9. The method of claim 8, wherein the at least one lactic acid bacteria used in step (a) of the process is a *Lactobacillus* species and the yeast used in step (a) of the process is a *Saccharomyces* species.

10. The method of claim 8, wherein the fermented soy extract is orally administered to the patient.

11. The method of claim 8, wherein the antibiotic treatment involves administration of a beta-lactam antibiotic to the patient.

12. The method of claim 11, wherein the antibiotic is selected from the group consisting of ampicillin, amoxicillin and a combination thereof.

13. A method to stimulate growth of lactic acid bacteria or bifidobacteria, comprising growing the lactic acid bacteria or bifidobacteria in a medium containing a fermented soy extract, wherein the fermented soy extract is made by a process comprising the steps of (a) fermenting an aqueous soy bean extract with at least one lactic acid bacteria and together with at least one yeast to form a fermented liquid: (b) sterilizing said fermented liquid: (c) filtering said sterilized fermented liquid: and (d) removing water from said filtered fermented liquid to form a concentrated fermented soy extract.

14. The method of claim 13, wherein the beneficial bacteria are *L. rhamnosus, L. paracasei, L. delbrueckii, B. infantis, B. lactis* Bb-12 or *B. longum*.

* * * * *